United States Patent

Alas et al.

[11] Patent Number: 5,856,581
[45] Date of Patent: Jan. 5, 1999

[54] PREPARATION OF CYCLIC KETONES

[75] Inventors: Michel Alas, Melle; Michel Crochemore, Chaponost, both of France

[73] Assignee: Rhone-Poulenc Chimie, Courbevoie Cedex, France

[21] Appl. No.: 251,112

[22] Filed: May 31, 1994

[30] Foreign Application Priority Data

May 28, 1993 [FR] France .................. 93 06476

[51] Int. Cl.$^6$ .................................... C07C 45/45
[52] U.S. Cl. ............................................. 568/355
[58] Field of Search ...................... 568/355, 397

[56] References Cited

U.S. PATENT DOCUMENTS 4,822,920  4/1989  Lerner et al. ................ 568/355

*Primary Examiner*—James H. Reamer
*Attorney, Agent, or Firm*—Burns, Doane, Swecker & Mathis, L.L.P.

[57] ABSTRACT

Cyclic ketones, notably cyclopentanone and 2,2-dimethylcyclopentanone, are simply, economically and efficiently prepared, even on an industrial scale, by decarboxylating/cyclizing a dicarboxylic acid, in liquid phase, in the presence of a catalytically effective amount of a metal or compound thereof selected from among boron, aluminum, gallium, indium, thallium, tin, antimony, bismuth, molybdenum, rubidium, cesium and vanadium.

40 Claims, No Drawings

PREPARATION OF CYCLIC KETONES

CROSS-REFERENCE TO COMPANION APPLICATION

Our copending application Ser. No. 08/251,271, filed concurrently herewith and assigned to the assignee hereof.

BACKGROUND OF THE INVENTION

1. Field of the Invention

The present invention relates to the preparation of cyclic ketones, and, more especially, to the preparation of cyclic ketones from dicarboxylic acids.

The present invention more particularly relates to the preparation of cyclopentanone from adipic acid and 2,2-dimethylcyclopentanone from 2,2-demethladipic acid.

2. Description of the Prior Art

GB-A-615,543 describes the preparation of cyclopentanone by heating adipic acid in the presence of manganese carbonate or oxide. The yield obtained in respect of cyclopentanone, when the cyclization reaction is carried out at 280° C., is excellent, on the order of 90%. However, this process is not completely satisfactory, as it is not possible to increase the level of cyclopentanone productivity. Indeed, to maintain the aforenoted levels of yield, it is necessary to limit the feedstream flow rates of adipic acid to about 0.7 kg/h per kilogram of catalyst. The feedstream flow rate could be increased by raising the reaction temperature.

Although the temperature indicated in GB-A-615,543 is said to range from 280° C. to 350° C., it is very difficult from an industrial standpoint to maintain a temperature of higher than 320° C. without using complex apparatus or special, expensive heat transfer fluids. In addition, it is very difficult, if not impossible, to maintain such a temperature homogeneous in the viscous medium which is constituted by the liquid adipic acid and the manganese-based catalyst. Too, other than the difficulties indicated above, risks are presented of the deposit of polymeric substrates on the reactor walls ("lining") which are difficult to remove.

Another process for the preparation of cyclopentanone via cyclization of adipic acid, in the presence of a magnesium oxide catalyst, is described in U.S. Pat. No. 2,612,524. This particular process also requires a high temperature, ranging from 300° C. to 350° C.

SUMMARY OF THE INVENTION

Accordingly, a major object of the present invention is the provision of an improved high-productivity process for the preparation of cyclic ketones that can simply and economically be carried out on an industrial scale and which does not require any sophisticated apparatus.

Briefly, the present invention features a process for the preparation of cyclic ketones, by decarboxylation and cyclization of a dicarboxylic acid having the following formula (I):

HOOC—R—COOH            (I)

in which R is a substituted or unsubstituted alkylene radical including a straight chain of atoms in sufficient number to form the desired ketonic ring member, said decarboxylation/cyclization reaction being carried out in the liquid phase, in the presence of a catalytically effective amount of a metal or compound thereof selected from among boron, aluminum, gallium, indium, thallium, tin, antimony, bismuth, molybdenum, rubidium, cesium, vanadium.

DETAILED DESCRIPTION OF BEST MODE AND PREFERRED EMBODIMENTS OF THE INVENTION

More particularly according to the present invention, it has now surprisingly been found that the subject catalysts, and preferably the compounds of tin and boron, are more active than the manganese-based catalysts. It is thus possible to increase the feed rate of dicarboxylic acid and especially adipic acid in a ratio of from 1 to 3 and indeed even 5.

According to the process of the invention, a dicarboxylic acid is used which corresponds to formula (I) in which R is a substituted or unsubstituted alkylene radical including a straight chain of atoms in sufficient number to form the desired ketonic ring member.

Generally, the radical R comprises a straight chain of from 2 to 10 atoms, preferably from 2 to 7 atoms, and even more preferably from 4 to 5 atoms. It typically comprises a chain of carbon atoms, but the invention does not exclude the hydrocarbon chain being interrupted by a heteroatom, in particular nitrogen, oxygen or sulfur.

As indicated above, the radical R may be substituted, namely, the hydrogen atoms of the hydrocarbon chain may be replaced by a substituent or functional group. Any substituents may be present so long as they do not interfere with the decarboxylation/cyclization reaction. In particular, the hydrocarbon chain may be substituted by side or branched chains, preferably by alkyl radicals generally having from 1 to 4 carbon atoms. The branched chains are typically situated on one or the two carbon atoms in the α- or β-position to the carboxylic groups.

In general, the radical R has a total number of carbon atoms which can vary broadly from 2 carbon atoms to a number as high as 40 carbon atoms when substituents are present and said radical comprises a straight chain of from 2 to 10 atoms which constitute the ring member thus formed.

In the formula (I), R is preferably a branched or straight alkylene radical, more preferably a branched or straight alkylene radical having from 2 to 20 carbon atoms.

The dicarboxylic acids of general formula (I) in which the aliphatic radical R is a branched or straight alkylene radical having from 2 to 12 carbon atoms and which comprises a straight chain of from 2 to 8 carbon atoms between the two COOH groups are very well suited for carrying out the process of the invention.

The preferred radical R comprises a straight chain of from 4 to 5 carbon atoms between the two COOH groups.

In the process of the invention, a dicarboxylic acid of formula (I) can be used in which R is a branched or straight alkylene radical wherein two adjacent carbon atoms can form a ring member.

By the term "ring" or "ring member" is intended a saturated or aromatic carbocyclic or heterocyclic ring.

Exemplary such rings are cycloaliphatic, aromatic or heterocyclic rings, in particular cycloalkyl rings having 6 carbon atoms in the ring, or benzene rings, such rings themselves optionally bearing one or more substituents, as long as they do not interfere with the decarboxylation/cyclization reaction.

Exemplary such radicals R include, e.g., the following:

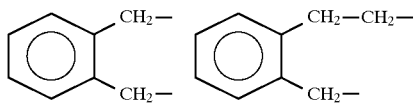

Among the carboxylic acids of formula (I) which are suitable according to the present invention, particularly representative are the following dicarboxylic acids:

Adipic acid,
2-Methyladipic acid,
3-Methyladipic acid,
4-Methyladipic acid,
5-Methyladipic acid,
2,2-Dimethyladipic acid,
3,3-Dimethyladipic acid,
2,2,5-Trimethyladipic acid,
2,5-Dimethyladipic acid,
Pimelic (heptanedioic) acid,
2-Methylpimelic acid,
2,2-Dimethylpimelic acid,
3,3-Dimethylpimelic acid,
2,5-Dimethylpimelic acid,
2,2,5-Trimethylpimelic acid,
Azelaic acid,
Sebacic acid, and
1,2-Phenylenediacetic acid In accordance with the process of the invention, the cyclization of the dicarboxylic acid is carried out in the presence of a boron based catalyst or a catalyst based on the aforesaid metallic elements: aluminum, gallium, indium, thallium, tin, antimony, bismuth, molybdenum, rubidium, cesium, vanadium.

These can be employed in any form. They can be present in the metallic state, or as an oxide or salt, whether simple or double salt, whether organic or inorganic.

The catalyst is advantageously a boron based catalyst.

Particularly exemplary thereof are boron compounds such as boric acids, e.g., orthoboric acid (or its precursor $B_2O_3$), metaboric acid, pyro- or tetraboric acid, or metallic borates, in particular of alkali metals, alkaline earth metals or ammonium, in anhydrous or hydrated state, in particular one-third borates, hemiborates, monoborates, diborates, triborates, tetraborates and pentaborates of metals, preferably alkali metals, or ammonium.

A double salt containing boron can also be used, in particular metallic fluoborates, for example potassium fluoborate.

Exemplary compounds of boron which are suitable according to this invention are:

Orthorhombic acid or precursor thereof,
Sodium metaborate,
Tetrahydrated sodium metaborate,
Sodium tetraborate,
Decahydrated sodium tetraborate or borax,
Pentahydrated sodium tetraborate,
Potassium metaborate,
Tetrahydrated potassium pentaborate,
Octahydrated potassium tetraborate,
Tetrahydrated ammonium pentaborate, and
Tetrahydrated ammonium tetraborate.

Preferably, sodium or potassium metaborate is used.

The metallic elements indicated above may be used in the metallic state, or in the form of an oxide or a hydroxide. An inorganic salt can be used, preferably a nitrate, sulfate, oxysulfate, halide, oxyhalide, silicate, carbonate or oxalate, as can an organic salt, preferably an acetylacetonate, an alcoholate and even more preferably a methylate or ethylate, a carboxylate and even more preferably an acetate.

The catalyst may be selected from among the metallic elements of Group 3b of the Periodic Table, thus including aluminum, gallium, indium and thallium.

By "Periodic Table" is intended that published in the *Bulletin de la Société Chimigue de France, No*, 1 (1966).

With respect to aluminum, any one of the various derivatives of aluminum can be used and more particularly one of the following compounds:

Aluminum nitrate,
Aluminum oxalate,
Oxides of aluminum in anhydrous, α- or β-form, or in monohydrate or trihydrate state,
Aluminum orthophosphate or metaphosphate,
Aluminum propoxide,
Aluminum silicate,
Hydrated or unhydrated aluminum sulfate.

The following are particularly exemplary of suitable compounds of gallium:

Gallium acetate,
Gallium acetylacetonate,
Gallium halides, for example gallium fluoride, chloride or bromide,
Gallium sesquioxide in anhydrous or hydrated form,
Gallium nitrate, and
Gallium sulfate in anhydrous or hydrated form.

Suitable derivatives of indium include the following preferred compounds:

Indium halides, for example indium fluoride, chloride or bromide,
Indium hydroxide In(OH),
Indium monoxide,
Indium sesquioxide in anhydrous or hydrated form,
Indium nitrate, and
Indium sulfate in anhydrous or hydrated form.

The following are exemplary derivatives of thallium:

Thallium acetate,
Thallium carbonate,
Thallium methoxide,
Thallium ethoxide,
Thallium halides, for example thallium mono- or trifluoride, mono- or trichlorochloride or mono- or tribromide,
Thallium hydroxide Tl(OH),
Thallium I or III oxide,
Thallium sesquioxide in anhydrous or hydrated form,
Thallium I or III nitrate,
Thallium oxalate,
Thallium III orthophosphate,
Thallium III hydrogenophosphate,
Thallium III pyrophosphate,
Thallium I or III sulfate,
Thallium II hydrogenosulfate, and
Thallium tartrate.

In addition to the elements of Group 3b of the Periodic Table, tin compounds can be used and more preferably the following:

Tin II acetate,
Tin halides, for example tin II or IV fluoride, chloride or bromide,
Tin II or IV oxides in anhydrous or hydrated form,
Tin II or IV nitrate or basic tin II nitrate,
Tin II orthophosphate,
Tin II metaphosphate,
Tin II pyrophosphate,
Tin II or IV sulfate,
Sodium stannate, and
Tin tartrate.

The following are exemplary antimony-based catalysts:
Antimony halides, for example antimony III or V fluoride, chloride or bromide,
Antimony III or V oxides in anhydrous or hydrated form,
Antimony III oxychloride,
Antimony III oxysulfate,
Basic antimony nitrate,
Antimony III sulfate, and
Antimony tartrate.

Another type of catalyst suitable for the process of the invention are derivatives of bismuth and more preferably the following compounds:

Bismuth I acetate,
Bismuth carbonate $Bi_2O_2CO_3$,
Bismuth citrate,
Bismuth halides, for example bismuth trifluoride, tri- or tetrachloride or tribromide,
Bismuth lactate,
Bismuth nitrate or basic bismuth nitrate $BiONO_3 \cdot H_2O$,
Bismuth oxalate,
Bismuth hydroxide,
Bismuth oxides in particular bismuth monoxide, trioxide, tetraoxide or pentaoxide in anhydrous or hydrated form,
Bismuth oxyhalides such as bismuth oxyfluoride, oxychloride and oxybromide,
Bismuth orthophosphate,
Basic bismuth salicylate,
Bismuth sulfate, and
Bismuth tartrate.

And the following are particularly exemplary molybdenum-based catalysts:

Molybdenum halides, for example molybdenum hexafluoride, molybdenum tri-, tetra- or pentachloride and molybdenum di-, tri- or tetrabromide,
Molybdenum hydroxides $Mo(OH)_3$, $MoO(OH)_3$ or $Mo_2O_3 \cdot 3H_2O$,
Molybdenum oxides such as molybdenum dioxide, trioxide, pentaoxide or sesquioxide,
Molybdenum oxyhalides such as molybdenum oxydifluoride or oxytetrafluoride, molybdenum oxydichloride, oxytrichloride, oxytetrachloride and oxypentachloride, molybdenum acid oxychloride and molybdenum oxydibromide,
Molybdenum metaphosphate, and
Ammonium molybdate.

As regards the rubidium catalysts, the following are exemplary:

Rubidium acetate,
Rubidium halides, for example rubidium I or III fluoride, chloride or bromide,
Rubidium carbonate or acid carbonate,
Rubidium hydroxide,
Rubidium oxides such as rubidium monoxide, sesquioxide, tetraoxide and peroxide,
Rubidium nitrate,
Rubidium sulfate,
Rubidium hydrogenosulfate, and
Rubidium tartrate.

Yet other catalysts which can be used in the process of the invention are the cesium-based catalysts and more especially the following compounds:

Cesium acetate,
Cesium halides, for example cesium fluoride, chloride or bromide,
Cesium oxides such as cesium trioxide or peroxide,
Basic cesium nitrate,
Acid cesium nitrate,
Cesium sulfate,
Cesium hydrogenosulfate, and
Cesium tartrate.

Derivatives of vanadium are also suitable for carrying out the process of the invention and more particularly the following compounds:

Vanadium halides such as vanadium tri-, tetra- or pentafluoride, vanadium di-, tri- or tetrachloride and vanadium tribromide,
Vanadium oxides such as vanadium oxide, vanadium dioxide, vanadium sesquioxide and vanadium pentaoxide,
Vanadium oxyhalides, in particular vanadium oxydi- or trifluoride, vanadium oxymono-, di- or trichloride and vanadium oxymono-, di- or tribromide,
Vanadium sulfate,
Vanadyl sulfate, and
Vanadyl acetylacetonate.

As indicated above, double salts of the elements of the invention can be used.

The following double salts suitable for the process of the invention are representative:

Thallium and aluminum sulfate $TlAl(SO_4)_2 \cdot 12H_2O$,
Thallium metavanadate $TlVO_3$,
Thallium pyrovanadate $Tl_4V_2O_7$,
Thallium molybdate,
Bismuth vanadate,
Bismuth molybdate,
Aluminum and rubidium sulfate $RbAl(SO_4)_2 \cdot 12H_2O$,
Rubidium borofluoride,
Vanadium and rubidium sulfate $RbV(S_4)_2 \cdot 12H_2O$,
Aluminum and cesium sulfate $CsAl(SO_4)_2 \cdot 12H_2O$,
Cesium borofluoride, and
Vanadium and cesium sulfate $CsV(SO_4)_2 \cdot 12H_2O$.

Among the catalysts indicated above, the more readily available are the preferred. Thus, the following catalysts are more particularly employed: sodium or potassium tetraborate; orthoboric acid; tin oxide; sodium or potassium stannate; bismuth, cesium or rubidium carbonate; molybdenum, aluminum, indium or antimony oxide; and thallium acetate.

In accordance with the process of the invention, the dicarboxylic acid is intimately contacted with one of the indicated catalysts. Mixtures of catalysts can of course also be used.

The catalysts of the invention, being active at low temperature, the subject process is carried out in liquid phase, preferably in the presence of a reaction solvent.

The dicarboxylic acid can itself be used as a reaction solvent, but preferably an organic solvent is used as a thermal transfer flux.

A number of requirements govern the selection of the organic solvent.

It must be stable under the reaction conditions and inert with respect to the starting material carboxylic acid and the cyclic ketone final product.

It must have a high boiling point, preferably from 200° C. to 500° C.

Particularly exemplary solvents which are suitable according to the present invention include the following:

(a) aliphatic and/or aromatic hydrocarbons and more particularly paraffins such as, in particular, decane, undecane, dodecane or tetradecane; aromatic hydrocarbons such as, in particular, xylenes, cumene, and petroleum cuts comprising a mixture of alkyl benzenes, in particular cuts of the Solvesso® type, (b) heavy esters of inorganic acids (for example tricresyl phosphate) or carboxylic acids (for example octyl phthalate), (c) ethers and more particularly aromatic ethers, such as biphenyl oxide and/or benzyl oxide, and (d) paraffinic and/or naphthenic oils, petroleum distillation residues.

A mixture of organic solvents can also be employed.

The process of the invention therefore entails use of the starting material dicarboxylic acid, the catalyst for the reaction and the organic solvent.

The concentration of dicarboxylic acid in the reaction mass may vary widely. In general, the dicarboxylic acid constitutes from 20% to 50% of the weight of the reaction mass/medium.

The amount of catalyst used, expressed in terms of the number of atoms of metallic cation per 100 moles of dicarboxylic acid, advantageously ranges from 0.1% to 20%, preferably from 1% to 10%.

From a practical point of view, when the process of the invention is carried out discontinuously, the procedure generally comprises first introducing the reaction solvent and the catalyst, followed by addition of the dicarboxylic acid, preferably in premelted state (molten).

The process of the invention can be carried out both discontinuously and continuously. In the former event, only the dicarboxylic acid is supplied.

The feedstream dicarboxylic acid flow rate can vary widely, e.g., from 0.1 to 4.0 kg/hour per kilogram of catalyst introduced. It preferably ranges from 0.5 to 1.0 kg/hour and per kilogram of catalyst.

The process of the invention is advantageously carried out at a temperature below 300° C., preferably ranging from 200° C. to 300° C. and more preferably from 250° C. to 290° C.

It is generally carried out at atmospheric pressure, but can also be conducted under a reduced pressure of, for example, from 50 to 760 mm of mercury A preferred embodiment of the process of the invention comprises the elimination by distillation, as they are formed, of the cyclic ketone, the carbon dioxide gas and the water.

At the end of the reaction, the cyclic ketone is recovered from the distillate using conventional procedures, in particular by settling or crystallization.

The process of the invention is well suited for the preparation of cyclopentanone, 2,2-dimethylcyclopentanone and cyclohexanone.

In order to further illustrate the present invention and the advantages thereof, the following specific examples are given, it being understood that same are intended only as illustrative and in nowise limitative.

In said examples to follow, the following abbreviations are employed:

RAH=ratio of hourly feed of adipic acid with respect to the catalyst $$RAH = \frac{\text{hourly charge of adipic acid (by weight)}}{\text{charge of catalyst (by weight)}}$$

$$TT = \frac{\text{number of moles of adipic acid converted}}{\text{number of moles of adipic acid introduced}} \%$$

$$RT = \frac{\text{number of moles of cyclopentanone formed}}{\text{number of moles of adipic acid converted}} \%$$

EXAMPLES 1 TO 10

The following Examples were carried out employing a continuous mode of operation.

The operating procedure employed in all Examples is more fully described below.

The apparatus used was always the same. It was a 1,000 ml glass balloon flask provided with a magnetic agitation means and surmounted by a Rashig column measuring 20 mm in diameter and 100 mm in height. The column head comprised a pouring funnel heated with a hot air jet for supplying the adipic acid which was melted beforehand.

The reaction solvent and the catalyst were introduced and then the molten adipic acid was added.

Continuous distillation of the cyclopentanone was effected at 130° C. at the column head, feeding the adipic acid onto the solvent/catalyst mixture which was maintained at a temperature of 250° C.

The different amounts of adipic acid and catalyst which were introduced are reported in the Table I which follows.

The nature of the reaction solvent is also reported in Table I. The volume of solvent was 500 ml. The Nyflex 810 used in Example 7 was a mixture of aromatic hydrocarbons (10%), naphthenic hydrocarbons (48%) and paraffinic hydrocarbons (42%).

At the end of the reaction, a distillate was recovered, comprising water and the cyclopentanone. The water was separated from the cyclopentanone by saturating the distillate with sodium chloride. The cyclopentanone was analyzed by gaseous phase chromatography.

As regards the distillation bottoms, it was extracted with 3×600 ml of a mixture of water and sodium hydroxide (60/40 by volume). The total volume was adjusted to 2,000 ml. 10 ml were drawn off, adjusted to 100 ml with a mixture of water/sodium hydroxide (15/85 by volume) containing 0.035% of phosphoric acid. The unconverted adipic acid was analyzed by high-performance liquid chromatography.

The tests were carried out in accordance with the operating procedure described above.

All of the operating conditions and results obtained are reported in the following Table I:

TABLE I

| Example | Solvent Nature | Volume (ml) | Catalyst Nature | Weight (g) | Adipic acid introduced Total (g) | /h | RAH | Time (h) | Acid remaining (g) | Cyclopentanone Weight (g) | RT (%) |
|---|---|---|---|---|---|---|---|---|---|---|---|
| 1 | biphenyl oxide | 450 | Na$_2$B$_4$O$_7$ | 8.08 | 417 | 17.4 | 2.15 | 16 | 21 | 208.5 | 91.5 |
|   | benzyl oxide | 50 | | | | | | | | | |
| 2 | dodecane tetradecane | 350 150 | Na$_2$B$_4$O$_7$ | 8.1 | 149 | 9.3 | 1.15 | 16 | 84 | 26.2 | 70 |
| 3 | biphenyl oxide | 450 | H$_3$BO$_3$ | 10.6 | 237.1 | 23.7 | 2.37 | 10 | 0.7 | 87.3 | 64.2 |
|   | benzyl oxide | 50 | | | | | | | | | |
| 4 | biphenyl oxide | 450 | Ga$_2$O$_3$ | 10 | 297 | 18.6 | 1.86 | 16 | 69 | 99.5 | 75.7 |
|   | benzyl oxide | 50 | | | | | | | | | |
| 5 | biphenyl oxide | 450 | Sn | 9.5 | 117.2 | 7.3 | 0.77 | 16 | 17.7 | 46 | 80.3 |
|   | benzyl oxide | 50 | | | | | | | | | |
| 6 | biphenyl oxide | 450 | SnO | 10.8 | 413.8 | 34.5 | 3.2 | 12 | 0 | 199.1 | 83.6 |
|   | benzyl oxide | 50 | | | | | | | | | |
| 7 | Nyflex 810 | 460 | SnO | 10.8 | 414.2 | 25.9 | 2.4 | 16 | 0 | 146.7 | 61.5 |
| 8 | dodecane tetradecane | 300 200 | SnO | 10.8 | 198.2 | 12.4 | 1.15 | 16 | 71.2 | 45.6 | 62.4 |
| 10 | biphenyl oxide | 450 | (BiO)$_2$CO$_3$ | 8 | 200 | 12.5 | 1.56 | 16 | 116 | 33.7 | 70.0 |
|   | benzyl oxide | 50 | | | | | | | | | |

EXAMPLES 11 TO 18

A series of tests entailing a discontinuous mode of operation was carried out.

The following materials were introduced into a 250 ml reactor provided with a magnetic agitation means and surmounted by a packed Multiknit column which was 20 mm in diameter and 100 mm in height, heat-insulated and equipped with a column head:

(i) the reaction solvent, which was biphenyl oxide, in a proportion of 140 ml, (ii) the catalyst whose nature is reported in Table II, in a proportion of 0.01 mole, and (iii) the molten adipic acid, namely, 0.2 mole (29.2 g).

The reaction mixture was placed under light reflux such that the vapors did not extend beyond the bottom of the column.

The cyclopentanone formed was distilled at the column head at a temperature equal to 130° C. until exhaustion occurred.

The duration of the operation was 8 hours.

The results obtained are reported in Table II:

TABLE II

| Example | Catalyst Nature | Weight (g) | TT (%) | RT (%) |
|---|---|---|---|---|
| 11 | Rb$_2$CO$_3$ | 2.31 | 78 | 81 |
| 12 | Cs$_2$CO$_3$ | 1.68 | 90 | 92 |
| 13 | NaVO$_3$ | 1.22 | 42 | 61 |
| 14 | MO$_3$ | 1.44 | 87 | 88 |
| 15 | Al$_2$O$_3$ | 1.02 | 65 | 73 |
| 16 | In$_2$O$_3$ | 2.77 | 77 | 83 |
| 17 | Tl(CH$_3$COO) | 2.63 | 69 | 78 |
| 18 | Sb$_2$O$_3$ | 2.91 | 45 | 66 |

EXAMPLE 19

5 g of 2,2-dimethyladipic acid were heated in the presence of 1.09 g of borax Na$_2$B$_4$O$_7$ and 17 ml of biphenyl oxide were added at 225° C. over 1 hour, 35 min.

The distillate, cooled to about 0° C., comprised two phases. After eliminating the water by absorption on sodium sulfate, the 2,2-dimethylcyclopentanone obtained was determined by gaseous phase chromatography.

The distillation bottoms was washed with an aqueous basic solution (3×100 ml of an aqueous solution of sodium hydroxide 1N) to extract the unconverted acid.

Quantitative determination by high-performance liquid chromatography provided the following results:

(a) TT$_{adipic\ acid}$=87%, (b) RT$_{2,2\text{-}dimethylcyclopentanone}$=92%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a cyclic ketone, comprising decarboxylating/cyclizing a dicarboxylic acid, in liquid phase, in the presence of a catalytically effective amount of a metal or compound thereof selected from among boron, aluminum, gallium, indium, thallium, tin, antimony, bismuth, molybdenum, rubidium, cesium and vanadium.

2. The process as defined by claim 1, said dicarboxylic acid having the formula:

HOOC—R—COOH  (I)

in which R is a substituted or unsubstituted alkylene radical including a straight chain of atoms in sufficient number to form the desired ketonic ring member.

3. The process as defined by claim 2, wherein formula (I), the radical R comprises a straight chain of from 2 to 10 atoms.

4. The process as defined by claim 3, wherein formula (I), the radical R comprises a straight chain of 4 or 5 atoms.

5. The process as defined by claim 2, wherein formula (I), the radical R is substituted.

6. The process as defined by claim 5, wherein formula (I), the radical R comprises at least one lower alkyl branch substituent.

7. The process as defined by claim 6, wherein formula (I), said at least one branch substituent is situated on one or the two carbon atoms in the $\alpha$- or $\beta$-position to the carboxylic groups.

8. The process as defined by claim 3, wherein formula (I), the radical R has from 2 to 40 carbon atoms.

9. The process as defined by claim 8, wherein formula (I), the radical R has from 2 to 12 carbon atoms.

10. The process as defined by claim 1, said dicarboxylic acid comprising adipic acid, 2-methyl adipic acid, 3-methyladipic acid, 4-methyladipic acid, 5-methyladipic acid, 2,2-dimethyladipic acid, 3,3-dimethyladipic acid, 2,2,5-trimethyladipic acid, 2,5-dimethyladipic acid, pimelic (heptanedioic) acid, 2-methylpimelic acid, 2,2-dimethylpimelic acid, 3,3-dimethylpimelic acid, 2,5-dimethylpimelic acid, 2,2,5-trimethylpimelic acid, azelaic acid, sebacic acid, or 1,2-phenylenediacetic acid.

11. The process as defined by claim 10, said dicarboxylic acid comprising adipic acid or 2,2-dimethyladipic acid.

12. The process as defined by claim 1, said active catalyst being in the metallic state, or in an oxide or salt form thereof.

13. The process as defined by claim 12, said active catalyst being in salt form, either simple or double salt, either inorganic or organic.

14. The process as defined by claim 1, said active catalyst comprising boron values.

15. The process as defined by claim 1, said active catalyst comprising aluminum values.

16. The process as defined by claim 1, said active catalyst comprising gallium values.

17. The process as defined by claim 1, said active catalyst comprising indium values.

18. The process as defined by claim 1, said active catalyst comprising thallium values.

19. The process as defined by claim 1, said active catalyst comprising tin values.

20. The process as defined by claim 1, said active catalyst comprising antimony values.

21. The process as defined by claim 1, said active catalyst comprising bismuth values.

22. The process as defined by claim 1, said active catalyst comprising molybdenum values.

23. The process as defined by claim 1, said active catalyst comprising rubidium values.

24. The process as defined by claim 1, said active catalyst comprising cesium values.

25. The process as defined by claim 1, said active catalyst comprising vanadium values.

26. The process as defined by claim 14, said boron values comprising a boric acid or precursor thereof, or a metal or ammonium borate, either hydrated or in anhydrous state.

27. The process as defined by claim 1, said active catalyst comprising sodium or potassium tetraborate; orthoboric acid; tin oxide; sodium or potassium stannate; bismuth, cesium or rubidium carbonate; molybdenum, aluminum, indium or antimony oxide; or thallium acetate.

28. The process as defined by claim 1, carried out in the presence of a reaction solvent.

29. The process as defined by claim 28, said reaction solvent comprising an aliphatic and/or aromatic hydrocarbon, a heavy ester of an inorganic or organic acid, an ether, a paraffinic and/or naphthenic oil, or a residue of petroleum distillation.

30. The process as defined by claim 1, wherein the concentration of dicarboxylic acid in the medium of reaction ranges from 20% to 50% by weight thereof.

31. The process as defined by claim 1, wherein the amount of said active catalyst, expressed as the number of atoms of metallic cation per 100 moles of said dicarboxylic acid, ranges from 0.1% to 20%.

32. The process as defined by claim 31, wherein the amount of active catalyst ranges from 1% to 10%.

33. The process as defined by claim 28, comprising introducing said reaction solvent and said active catalyst into a reaction zone and then adding said dicarboxylic acid thereto.

34. The process as defined by claim 33, the dicarboxylic acid added being in molten state.

35. The process as defined by claim 1, comprising reacting from 0.1 to 4.0 kg/hour of said dicarboxylic acid per kilogram of active catalyst.

36. The process as defined by claim 35, comprising reacting from 0.5 to 1.0 kg/hour of said dicarboxylic acid per kilogram of active catalyst.

37. The process as defined by claim 1, carried out at a temperature ranging from 200° to 300° C.

38. The process as defined by claim 1, comprising the preparation of cyclopentanone.

39. The process as defined by claim 1, comprising the preparation of 2,2-dimethylcyclopentanone.

40. The process as defined by claim 1, comprising the preparation of cyclohexanone.

* * * * *